United States Patent [19]

Simon

[11] Patent Number: 5,023,374
[45] Date of Patent: Jun. 11, 1991

[54] DICARBOXYLIC ACID DIAMIDES, PROCESS FOR THEIR PREPARATION, ION SELECTIVE MEMBERS AND TEST MEANS CONTAINING THEM AS WELL AS LITHIUM COMPLEXES OF THE DICARBOXYLIC ACID AMIDES

[75] Inventor: Wilhelm Simon, Zürich, Switzerland

[73] Assignee: Firma Willi Möller, Zurich, Switzerland

[21] Appl. No.: 586,323

[22] Filed: Sep. 19, 1990

Related U.S. Application Data

[63] Continuation of Ser. No. 99,579, Sep. 22, 1987, abandoned.

[30] Foreign Application Priority Data

Sep. 23, 1986 [CH] Switzerland .................... 3795/86

[51] Int. Cl.⁵ .......................................... C07C 235/14
[52] U.S. Cl. .................................................. 564/152
[58] Field of Search ..................................... 564/152

[56] References Cited

U.S. PATENT DOCUMENTS 4,785,111 11/1988 Toda .............................. 564/152 X

FOREIGN PATENT DOCUMENTS 0174572 8/1985 European Pat. Off. .

OTHER PUBLICATIONS

Metzger et al, Helv. Chim. Acta, 69(8), 1021-8 (1986).
Metzger et al, Analytical Chemistry, 59(13), 1600-3 (1987).
Vatlina et al, CA 88:89174x (1978).
*Chemical Abstracts*, vol. 98, No. 3, p. 207, Abstract No. 13059z (Jan. 17, 1983); Margalit et al., *Pfluegers Arch.*, 395(2), 87-92 (1982).
*Chemical Abstracts*, vol. 102, No. 11, p. 539, Abstract No. 95269f (Mar. 18, 1985); Israel Pat. App. 59,148, Jan. 31, 1984 (Yeda Research and Dev. Co., Ltd.).
Zhukov et al., *Analytica Chimica Acta*, 131, 117-122 (1981).
Erne et al., *Helv. Chim. Acta*, 65, 538-545 (1982).

*Primary Examiner*—Carolyn S. Elmore
*Attorney, Agent, or Firm*—Seidel, Gonda, Lavorgna & Monaco

[57] ABSTRACT

Dicarboxylic acid diamides having the formula I

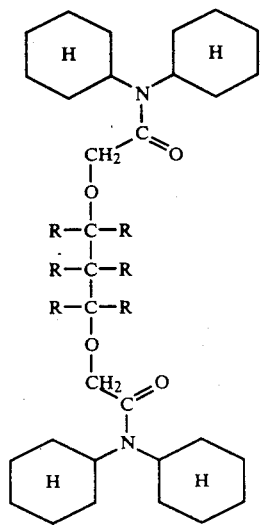

wherein the radicals R are selected from hydrogen, alkyl, alkenyl and alkynyl with up to 20 carbon atoms, have a high selectivity for lithium ions over other alkali metal ions and alkaline earth metal ions. Ion selective membranes and ion selective coatings as well as ion selective test devices, like e.g. test strips, which contain said compounds of formula I as ion selective component, can be used for the determination of lithium ions in liquid media. Said membranes and test devices are also suited for the determination of the concentration of lithium ions in biological fluids in which low concentrations of lithium ions and high concentrations of sodium ions are present, like the corresponding determination in blood serum or whole blood. The ion selective membranes have a period of life of several months even if they are frequently contacted with blood serum or blood.

Lithium complexes of the dicarboxylic acid diamides of formula I were prepared in crystalline form and the new carboxylic acid diamides of formula I were prepared by etherifying the corresponding diols.

14 Claims, No Drawings

DICARBOXYLIC ACID DIAMIDES, PROCESS FOR THEIR PREPARATION, ION SELECTIVE MEMBERS AND TEST MEANS CONTAINING THEM AS WELL AS LITHIUM COMPLEXES OF THE DICARBOXYLIC ACID AMIDES

This is a continuation of copending application Ser. No. 07/099,579 filed on Sept. 22, 1987 now abandoned.

BACKGROUND OF THE INVENTION

The present invention concerns dicarboxylic acid diamides, the amine component of which is dicyclohexylamine. Said dicarboxylic acid diamides form lithium complexes which are soluble in lipophilic solvents. The dicarboxylic acid diamides have a high selectivity for lithium ions compared with their selectivity for other alkali metal ions and alkaline earth metal ions. The dicarboxylic acid diamides can be used as ion selective component of ion selective membranes for the determination of the concentration of lithium ions and furthermore as component of test means, for instance test strips for the determination of lithium ions in liquid media.

A further object of the invention are processes for the preparation of the new dicarboxylic acid diamides.

DESCRIPTION OF THE PRIOR ART

In many publications dicarboxylic acid diamides are described which form lipophilic complexes with different cations and which can be used as components of ion selective membranes for the determination of the concentration of the cations in question. Among said prior art dicarboxylic acid diamides there are to be found also corresponding compounds which have a higher selectivity for lithium ions than for other alkali metal ions.

In Chemical Abstracts, volume 102, no. 11, March 18, 1985, page 539, abstract no. 95269f, Yeda Research and Development Co. there are described dicarboxylic acid diamides which have some selectivity for lithium ions. The amide forming amine component of said dicarboxylic acid diamides is a dialkylamine in which one of the two alkyl groups is unsubstituted and the other of said two alkyl groups is substituted with alkoxy groups, acyl groups, ester groups or amide groups. The lipophilic lithium complexes of said dicarboxylic acid diamides were injected intracerebrally into rats and through said administration the lithium ratio in the cortex of the animals was higher compared with a corresponding administration of lithium chloride to said animals.

The concentration of the most important cations which are to be found in biological fluids, i.e. the concentration of $Na^+$, $K^+$, $Ca^{2+}$ and hydrogen ions are usually determined in clinical laboratories by using electrodes which are equipped with a corresponding ion selective membrane for the determination of said ions. Contrary to this the corresponding tests for the determination of the concentration of lithium ions are until now performed using flame photometers or the atomic absorption spectrometry.

The determination of the concentration of lithium ions in the blood serum is of great importance if persons who suffer from manic-depressive psychosis are submitted to a therapeutic administration of lithium ions or if lithium ions are prophylactically administrated to persons in order to prevent the development of such manic-depressive psychosis. With regard to this we refer to the publication of A. Amidsen and M. Schou in "Münch. Med. Wochenschr.", 117(1975) 1417 and to the publication of A. Amidsen in Dan. Med. Bull., 22(1975) 277.

In the blood serum the concentration of sodium ions is far higher than the concentration of lithium ions. Electrodes, which are equipped with ion selective membranes for the determination of the activity or concentration of lithium ions have to have a high selectivity for lithium ions over other alkali metal ions, and specially over sodium ions, in order that said electrodes can be used for a determination of the concentration of lithium ions in the blood serum. An ion selective component of an ion selective membrane for the determination of lithium ions in body fluids, like blood serum, accordingly has to fulfil high requirements as to its $Li^+/Na^+$-selectivity. Furthermore electrodes which are equipped with such lithium selective membranes have to have a sufficient stability of the E.m.F.-response and furthermore the life period of said membranes has to be sufficiently long if the membranes are frequently contacted with blood serum or whole blood when used for the determination of the concentration of lithium ions.

Extended research work had already been done in order to prepare new diamides of dicarboxylic acids in order to provide new complex forming agents which have the required high selectivity for lithium ions over other alkaline metal ions and alkaline earth metal ions. Furthermore also tests were performed in order to determine whether or not said dicarboxylic acid diamides can be use as ion selective components of ion selective membranes for the determination of the concentration of lithium ions.

In Chemical Abstracts, volume 98, no. 3, Jan. 17, 1983, page 207, abstract no. 13059z lithium ion-selective ionophores are disclosed, which are dicarboxylic acid diamides and also the ion-selectivity of corresponding model membranes was tested. The amide forming amine of said dicarboxylic acid diamides is a substituted diheptylamine in which the heptyl groups can be substituted with substituents which are selected from the group comprising aliphatic ethers, tetrahydrofurane, esters and amides. The selectivity factor for lithium ions over sodium ions of the best of said dicarboxylic acid diamides however was only 13. This is completely insufficient if corresponding membranes containing said lithium selective component will be used for the determination of lithium ions in liquid media containing higher concentrations of sodium ions than lithium ions.

Electrodes having an ion selective membrane which contain as ion selective component dicarboxylic acid diamides which have a selectivity for lithium ions over sodium ions are described in the publication of A. F. Zhukov, D. Erne, D. Amman, M. Güggi, E. Pretsch and W. Simon in Analytica Chimica Acta, 131 (1981), pages 117–122. One of the dicarboxylic acid diamides described in said publication is a diclohexane-1,2-dicarboxylic acid diamide having the following formula A

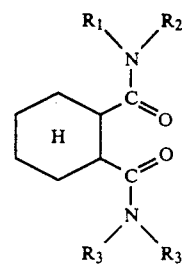

and in said specific compound the group of formula

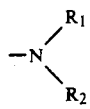

and also the group of formula

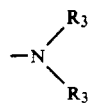

has the following structure:

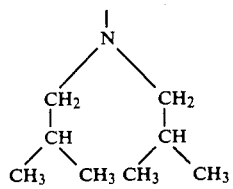

Of the dicarboxylic acid diamides of said publication the compound of formula A had the highest selectivity for lithium ions over sodium ions. The synthesis of said cyclohexane-1,2-dicarboxylic acid diamide of formula A is described in the publications of D. Erne, D. Ammann, A. F. Zhukov, F. Behm, E. Pretsch and W. Simon, in Helv. Chim. Acta, 65 (1982), pages 538–545.

In the European patent publication no. 0 174 572 there are described two specific compounds which are cyclohexane-1,2-dicarboxylic acid diamides and of all prior art compounds they had the highest selectivity for lithium ions over other alkali metal ions. Said two compounds correspond to the above stated formula A and the radical having the formula

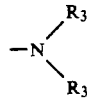

has the same structure as stated before for the compounds of formula A. Contrary to this the group having the formula

is in one of those two compounds a group having the structure

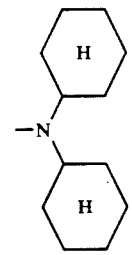

and in the other of those compounds a group having the following structure

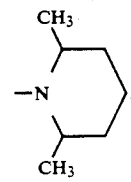

Ion selective membranes which contain as ion selection component one of the two cyclohexane-1,2-dicarboxylic acid diamides described in the European patent publication no. 0 174 572 and furthermore the o-nitrophenyl-n-octylether as plasticizer have a high selectivity for lithium ions over sodium ions, i.e. a value for $$\log K^{Pot}_{LiNa}$$

of $-2.3$. The corresponding value of the structurally closely related compound of formula A stated before is only $-1.0$.

Ion selective membranes which contain as ion selective component one of the two dicarboxylic acid diamides described in the stated European patent publication no. 0 174 572 and furthermore the rather polar plasticizer o-nitrophenyl-n-octylether can be used for the determination of lithiums ions in physiological fluids like blood serum or whole blood. The corresponding membranes however have only a period of life of a few weeks if they are frequently contacted with blood serum or whole blood. It is believed that the rather polar properties of the plasticizer respectively a migration of the plasticizer into the test solution due to the polar properties of the plasticizer resulted in the short period of life of said membranes. Attempts to avoid said deficiencies by using said two cyclohexane-1,2-dicarboxylic acid diamides in combination with less polar plasticizers however failed, because the corresponding membranes had no sufficient high selectivity for lithium ions over other alkali metal ions and corresponding membranes accordingly were not suited for a determination of lithium ions in biological fluids.

SUMMARY OF THE INVENTION

The object of the present invention was to provide new dicarboxylic acid diamides which have a high selectivity for lithium ions over other alkali metal ions and which can be used as ion selective component of corresponding ion selective membranes. Said membranes should have a long period of life if they are contacted with test solutions and specially also with biological fluids like e.g. blood serum or whole blood.

A further object of the present invention are processes for the preparation of said new dicarboxylic acid diamides and lithium complexes of said dicarboxylic acid diamides.

The invention furthermore concerns ion-selective membranes for the determination of the concentration of lithium ions and test means for the determination of the concentration of lithium ions which contain said dicarboxylic acid diamides as ion selective components.

It was quite unexpectedly found out that new dicarboxylic acid diamides fulful the necessary requirements and that said new dicarboxylic acid diamides are not at all structurally closely related to the two prior art compounds which had the highest selectivity for lithium ions known until now, i.e. the two cyclohexane dicarboxylic acid diamides described in the European patent publication no. 0 174 572. The dicarboxylic acid from which said new dicarboxylic acid diamides are derived is a dicarboxylic acid having a aliphatic chain comprising seven carbon atoms and two ether oxygen atoms.

DESCRIPTION OF THE INVENTION

One object of the present invention are new dicarboxylic acid diamides which have the following formula I

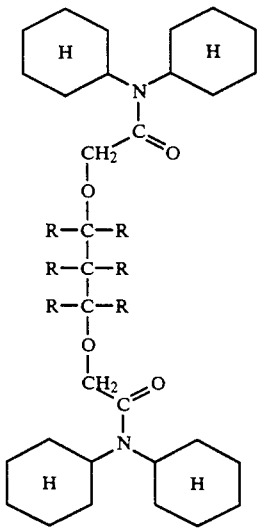

I wherein the radicals R have independently from each other the meaning of hydrogen atoms, straight chain or branched chain alkyl radicals having 1–20 carbon atoms, straight chain or branched alkenyl radicals having 2–20 carbon atoms or straight chain or branched alkynyl radicals having 2–20 carbon atoms.

Said new dicarboxylic acid diamides of formula I have a very high selectivity for lithium ions over sodium ions and using said dicarboxylic acid diamides of formula I as ion sensitive components lithium selective membranes can be prepared which have a long period of life even if they are frequently contacted with blood serum or whole blood.

In preferred inventive dicarboxylic acid diamides of formula 1 the radicals R have independently from each other the meaning of hydrogen atoms or straight chain or branched chain alkyl radicals having 1–15 carbon atoms, preferably straight chain or branched chain alkyl radicals having 1–8 carbon atoms.

In preferred dicarboxylic acid diamides of formula I furthermore at least two of the radicals R have the meaning of hydrogen atoms and preferably 3–6 of the radicals R have the meaning of hydrogen atoms. Preferably those radicals R which are not hydrogen atoms have the meaning of straight chain or branched chain alkyl radicals having 1–6 carbon atoms, for example 1–4 carbon atoms.

Specific examples for inventive dicarboxylic acid diamides comprised by the generic formula I are the compounds having the following formulae II through VI.

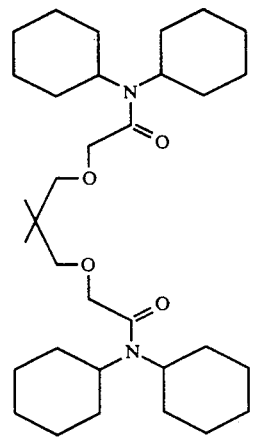

II

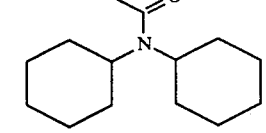

III

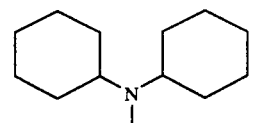

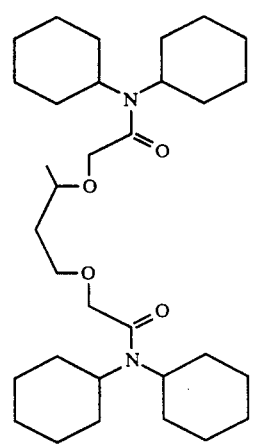

IV

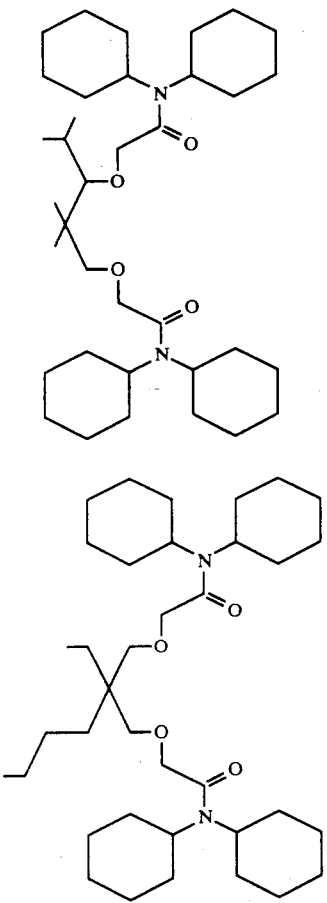

It can be seen from the structural formula I that in the inventive dicarboxylic acid diamides the amine component of the two acid amide groups is dicyclohexylamine. The high selectivity of said compounds of formula I for lithium ions over other alkali metal ions compared with corresponding compounds in which the acid amide forming amine is not dicyclohexylamine was not at all to be expected.

For comparison a dicarboxylic acid diamide was tested, in which the dicarboxylic acid has the same structure as the dicarboxylic acid of the inventive compounds of formula II stated before. In said dicarboxylic acid diamide for comparison, however, the amide forming amine component was not dicyclohexylamine but methyl-heptylamine. Said dicarboxylic acid diamide for comparison accordingly had the following formula B

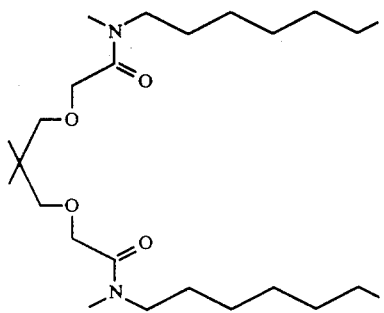

Said compound of formula B and further dicarboxylic acid diamides in which the amide forming dicarboxylic acid is identical to the dicarboxylic acid-moiety of the inventive dicarboxylic acid diamides having the formulae III, V and VI, in which however the amide forming amine group is methylheptylamine are disclosed in the publication of Zhukov et al. Analytica Chimica Acta, 131 (1981), pages 117-122 mentioned before. The best of the prior art compounds described in said publication had a selectivity coefficient for lithium ions over alkali metal ions of more than 100 and a selectivity coefficient for lithium ions over alkaline earth metal ions of about 1000. If said compounds, however, are used as ion selective component of ion selective membranes their selectivity coefficient for lithium ions over sodium ions is not sufficiently high so that said membranes could be used for the determination of lithium ions in biological fluids. In membranes having an analogous composition there was used as ion selective component on one hand the compound for comparison B described in said publication and the structurally closely related inventive compound of formula II stated before. In said test the value of $$\log K_{LiNa}^{Pot}$$

was $-1,2$ for the prior art compound B and $-1,7$ for the inventive compound of formula II.

A further object of the present invention is a process for the preparation of the new inventive dicarboxylic acid diamides of formula I

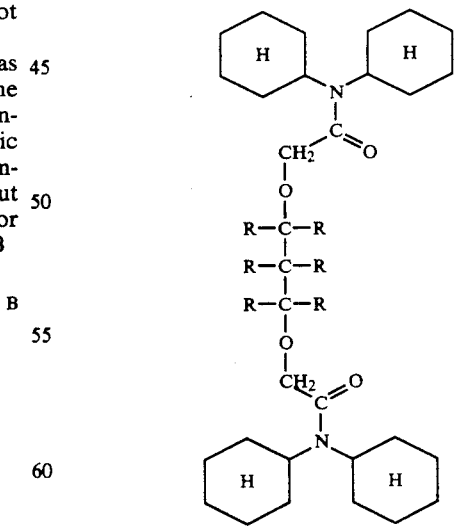

in which
the radicals R have the meaning stated before.
According to said new process a diol of formula VII

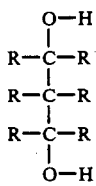

VII wherein the radicals R have the same meaning as in formula I
is either etherified with an acid amide having the formula VIII

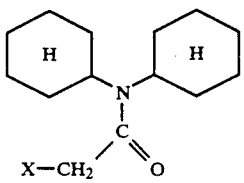

VIII wherein
X is a leaving group
to yield the dicarboxylic acid diamide of formula I, or the above stated diol having the formula VII is etherified with an ester having the formula IX

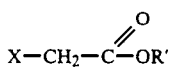

IX wherein
X is a leaving group and
R is an aliphatic, cycloaliphatic, aromatic or heterocyclic radical,
to yield a dicarboxylic diester having the formula X

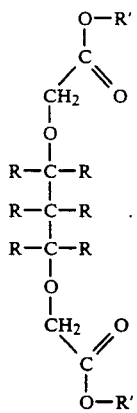

X

Thereafter said ester of formula X is either directly reacted with a dicyclohexyl amine having the formula XI

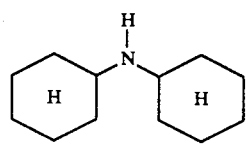

XI to yield the dicarboxylic acid amide of formula I or said ester is first saponified and converted to an active dicarboxylic acid derivative and thereafter reacted with the dicyclohexyl amine of formula XI yo yield the dicarboxylic acid diamide of formula I.

In said process the leaving group X of the starting material of formula VIII and the starting material of formula IX respectively has to activate the $CH_2$ group of the corresponding acetic acid amide of formula XIII or the $CH_2$ group of the corresponding acetic acid ester of formula IX sufficiently so that said compounds are able to ethrify the two hydroxy groups of the diol-starting material of formula VII. Examples for corresponding ester starting materials of of formula IX which can be used for the performance of said process are diazoacetic acid esters like e.g. diazo acetic acid ethyl ester.

The inventive dicarboxylio acid diamides of formulae II through VI stated before are prepared according to the above described process using as starting material corresponding diols of formula VII.

A further subject of the present invention are the lithium complexes of the dicarboxylic acid diamides having the formula I.

Furthermore lithium complexes of preferred compounds of formula I were prepared like the lithium complexes of the compounds having the formulae II through VI.

The X-ray analysis of said lithium complexes showed, that said complexes are 1:1 complexes, and that accordingly one lithium ion is complexed with 1 molecule of the complex forming agent of formula I.

The crystal structure of the complexes of LiNCS with the complex forming agent of formula II stated before was investigated. Thereby it was found out that the four oxygen atoms of the complex forming agent, i.e. the two etheroxygen atoms and the two carbonyloxygen atoms of the carboxylic acid diamides form the base of a slightly distorted quadratic pyramid. The $Li^+$ cation is situated 0,76 Angström above the base of said pyramid and to said lithium cation there is bonded the nitrogen atom of the NCS-anion. In said complex furthermore the mean distance between the lithium cation and the oxygen atom of the carbonyl group is 1.94 Å while the mean distance between the lithium cation and the oxygen atom of the ether group is 2.16 Å.

After said accurate investigation of the crystal structure of the inventive lithium complexes it is quite amazing that the inventive complex forming agent of formula I has a far higher selectivity for lithium ions over sodium ions than the complex forming agents disclosed in the publication of Zhukov et al. mentioned before, because the structural difference between the inventive compounds of formula I and the prior art compounds is to be found in the amine component of the acid amide and not in the structure of the dicarboxylic acid moiety of said acid amide. A person experienced in the art would rather conclude from the investigations of the crystal structure that the amine component of the dicarboxylic acid diamide has no important influence on the lithium over sodium selectivity of said compounds. The contrary, however, was true (see what is explained before) when the inventive compounds of formula II were compared with the prior art compounds of formula B.

A further object of the present invention is an ion selective membrane for the determination of the concentration of lithium ions, which membrane is characterized in that it comprises as ion selective component an inventive dicarboxylic acid diamide having the formula I stated before.

Preferred inventive ion selective membranes contain as ion selective component the preferred dicarboxylic acid diamides defined before which all are comprised by formula I, like e.g. the specific compounds having the formulae II through VI.

Preferred inventive ion selective membranes furthermore comprise poly(vinylchloride) as matrix for the ion selective component.

Usually the inventive ion selective membranes furthermore contain a plasticizer. The preferred plasticizers are lipophilic plasticizers and specially preferred are such plasticizers which are esters of dicarboxylic acids.

Using poly(vinylchloride) as matrix, a dicarboxylic acid diamide of formula I as ion selective component and furthermore the rather nonpolar plasticizer bis(1-butylpentyl)adipate ion selective membranes were prepared which were suited for the determination of lithium ions in blood serum, blood plasma and whole blood and which had a period of life of several months when used in said field of application.

Ion selective membranes which contained the inventive dicarboxylic acid diamides of formula I as ion selective component, poly(vinylchloride) as matrix and furthermore bis (1-butylpentyl)adipate as plasticizer usually had the following composition:

0.9–5.0% by weight, referred to the total weight of the membrane of the ion selective component of formula I, 64.9–67.3% by weight, referred to the total weight of the membrane of the bis (1-butylpentyl)adipate and 31.5–33.5% by weight, referred to the total weight of the membrane of poly(vinylchloride).

Specially preferred of the above stated ion selective membranes contain 1,2% by weight to 2,0% by weight, referred to the total weight of the membrane of the ion selective dicarboxylic acid diamide of formula I.

The EMF-measurements of the membranes containing the inventive compounds of formula I as ion selective component and of membranes for comparison were performed with macroelectrodes using the following type of cells:

Hg; $Hg_2Cl_2$, KCl (sat.) | 3 M KCl | sample solution || ion selective membrane || internal filling solution, AgCl; Ag.

The reference electrode was a double junction saturated calomel electrode, as already described in the publication of E. Metzger, D. Ammann, R. Asper, W. Simon, in Anal. Chem. 1986, 58, pages 132–135. Said double junction saturated calomel electrodes have a free-flowing free-diffusion liquid junction and a flow rate of 1 $\mu$l per hour. They are described in detail in the publication of R. E. Dohner, D. Wegmann, W. E. Morf, and W. Simon in Analytical Chemistry, 1986, 58, pages 2585–2589.

The internal filling solution was a 0.001 molar solution of LiCl and more details about the performance of the measurements and the mathematical evaluation of the results are disclosed in the above stated publication of E. Metzger et al.

The studies of blood serum and of sample solutions having a fixed ion background were carried out with minielectrodes using the following cell types:

Hg; $Hg_2Cl_2$, KCl (sat.) | 3 M $NH_4NO_3$ | sample solution- || ion selective membrane || internal filling solution AgCl; Ag.

Said ion selective minielectrode comprised a small electrode body of poly(methyl-methacrylate) with a vertical channel having an inner diameter of 0.8 mm. Into said channel the sample solution was injected from the top. The channel filled with the sample was contacted with one side of the ion selective membrane and the other side of the ion selective membrane was contacted with the internal filling solution. The internal reference was a silver wire coated with silver chloride. The internal filling solution was a solution of 0.001 M LiCl plus 0.14M NaCl plus 0.5% agar.

In said equipment the external reference electrode was a conventional macroelectrode as described in the above stated publication of E. Metzger et al., but equipped with a thin glass tip. The external reference electrode was dipped from above into the sample channel of the ion selective electrode body.

The sample solution was injected with a small glass syringe and after the measuring removed downwards by applying a vacuum. The volume of the sample channel was 0.1 ml.

After the sample had been injected it was measured during 4 minutes by taking the EMF-values in intervals of 20 seconds. A mean of at least six values was taken for further evalutation.

The ion selective membranes were perpared according to the process described by P. Anker; E. Wieland; D. Ammann; R. Dohner; R. Asper and W. Simon in Anal. Chem. 1981, 53, 1970. In the inventive membranes a compound of formula I was used as ion ion selective component and in the membranes for comparison prior art ion selective components were used. The matrix of the inventive membranes and the membranes for comparison was poly(vinylchloride) and optionally the membranes contained a plasticizer and further components already mentioned before.

When the EMF-measurements were performed with macroelectrodes using the cell type described before, then the ion selective membranes were mounted in a Philips electrode body, IS 560 (N. V. Philips, Eindhoven, Netherlands) and the electrodes were conditioned overnight in about 2 ml of the internal filling solution before use.

With the macroelectrodes and with the above described minielectrodes measurements were performed with inventive ion selective membranes containing as ion selective components the inventive compounds of formula I as well as the ion selective membranes which contained as ion selective component a prior art dicarboxylic acid diamide. With the inventive membranes and with the membranes for comparison the value $$\log K_{LiNa}^{Pot}$$

was determined.

A further object of the present invention is a test means for the determination of lithium ions in liquid media, which test means is characterized in that it comprises as component an inventive dicarboxylic acid diamide of formula I.

Corresponding test strips for the determination of the concentration of ions, which contain an ion selective component, are already described in the European patent publication 0 153 641.

The inventive test means preferably contain the ion selective component in a polymer matrix, for example of poly(vinylchloride). Preferably the test means contain as further component an indicator which indicates an alternation of the pH value. Said indicator for instance can be one of the well known pH indicators which indicate a change of the pH value by an alternation of their colour.

When such an inventive test means which contains as ion selective component an inventive dicarboxylic acid diamide of formula I is contacted with a liquid medium which contains lithium ions, then in the test means the complex between the lithium ions and the inventive compounds of formula I is formed. When said complex is formed, furthermore the pH value in the test means is changed and said alternation of the pH value is indicated by a corresponding colour change of the pH indicator.

The inventive test means can e.g. be test foils, test ribbons or test strips.

Using the inventive test means, like e.g. a corresponding test strip, lithium ions can be easily and rapidly detected in liquid media, for example in body fluids.

The following not limitative examples will illustrate processes for preparing inventive compounds of formula I, processes for the preparation of lithium complexes of the compounds of formula I as well as procedures for preparing ion selective membranes containing the inventive compounds. The examples furthermore will illustrate the performance of the EMF-measurements.

EXAMPLE 1

Preparation of the N,N,N',N'-tetracyclohexyl-5-butyl-5-ethyl-3,7-dioxa-azelaic-acid-diamide Said compound is the inventive compound having the formula VI stated before.

Step A

Preparation of the 5-butyl-5-ethyl-3,7-dioxa-acelaic-acid-diethylester 5.0 g (31.2 mmol) of 2-butyl-2-ethyl-1,3-propane diol (purum, Fluka AG, Buchs, Switzerland) and 6.5 ml (62.4 mmol) of ethyl diazo acetate (purum, Fluka AG) were added to 50 ml dried methylene chloride. Nitrogen gas was bubbled through the solution and it was cooled to a temperature of 0°–5° C. using an ice bath. 1 ml of boron-trifluoride-ethyl-etherate (pract., Fluka AG) was added slowly using an injection syringe. A violent reaction with nitrogen formation was observed.

After the total amount of the boron-trifluoride-ethyl-etherate had been added the solution was stirred for one hour at room temperature and thereafter refluxed at a temperature of 45° C. for 1½ hour. Then the solvent was evaporated. The remaining crude product was purified by flash-chromatography on silicagel (silicagel 6, Fluke AG) and the elution medium was a mixture of 8 parts of hexane and 2 parts of ethyl acetate.

6.08 g (18.3 mmol) of the product named in the title were recovered and the yield was accordingly 58.6% of the theoretical yield. The I.R. spectrum of the liquid showed a peak at 1755 cm$^{-1}$.

Step B

Preparation of the 5-butyl-5-ethyl-3,7-dioxa-azelaic acid 6.08 g (18.3 mmol) of the 5 butyl-5-ethyl-3,7-dioxa-azelaic acid diethylester were dissolved in 100 ml of a mixture of 4 parts of methanol and 1 part of water. 3.6 g (64 mmol) of potassium hydroxide (purum, Siegfried AG, Zofingen, Switzerland) were added and the mixture was refluxed at 80° C. for 19 hours.

After the reaction mixture had been cooled to room temperature 6 molar hydrochloric acid was added, until a pH value of about 1 was reached. Thereafter the solvents were evaporated and the residue extracted with acetone. The acetone solution was dried over magnesium sulfate and thereafter the solvent was removed under vacuum.

The yield was about 5 g (18 mmol), corresponding to more than 95% of the theoretical yield.

The I.R. spectrum in chloroform showed a broad peak in the range of 3500–2500 cm$^{-1}$, and a peak at 1720 cm$^{-1}$.

Step C

Preparation of the 5-butyl-5-ethyl-3,7-dioxa-azelaic acid dichloride 5.0 g (18.1 mmol) of the 5-butyl-5-ethyl-3,7-dioxa azelaic acid, 5.2 ml (72.4 mmol) of thionylchloride (purum, Fluka AG) and 3 drops of N,N-dimethylformamide (puriss. p.a., Fluka AG) were dissolved in 100 ml of toluene and the material refluxed at a temperature of 100°–120° C. for one hour. After the evaporation of the solvent the crude product was distilled under vacuum at a pressure of 0.08 mm and a temperature of 205° C.

The yield was 4.06 g (13.0 mmol), corresponding to 71.6% of the theoretical yield.

In the I.R. spectrum said liquid showed peaks at 1805 cm$^{-1}$ and 1750 cm$^{-1}$.

Step D

Preparation of the N,N,N',N'-tetracyclohexyl-5-butyl-5-ethyl-3,7-dioxa-azelaic acid-diamide 4.94 g (27.2 mmol) of dicyclohexylamine (puriss. p.a., Fluka AG) and 2.73 g (27.0 mmol) of triethylamine (anhydrous, Siegfried AG, Zofingen, Switzerland) were dissolved in 150 ml methylene chloride. 4.06 g (13.0 mmol) of 5-butyl-5-ethyl-3,7-dioxa-azelaic acid dichloride, dissolved in 20 ml methylene chloride were added slowly to the vigorously stirred solution. The mixture was stirred for 18 hours at room temperature and then washed several times with water.

The methylene chloride layer was dried over magnesium sulfate and the solvent evaporated. 5.6 g (9.3 mmol) of a crude product were recovered, corresponding to a yield of 71.5% of the theoretical yield. Said crude product was purified on a silicagel column which was filled with 240 g silicagel 60 of the Fluka AG. The yield of the selected fraction was 0.11 g (0.18 mmol), corresponding to a yield of said purified product of 1.4%, referred to the theoretical yield.

The I.R. spectrum in chloroform showed peaks at 3000 cm$^{-1}$, 2930 cm$^{-1}$ and 1630 cm$^{-1}$.

The NMR-spectrum ($^1$H-NMR) in CDCl$_3$ gave:
0.81 (t, 3H, CH$_3$CH$_2$CH$_2$CH$_2$); 0.88 (t, 3H, CH$_3$CH$_2$); 1.06–1.83 (m, 44H, CH$_2$ of the cyclohexyl rings and aliphatic chains; 2.40–2.47 (m, 4H, NCHCH$_2$); 2.87–2.93 (m, 2H, NCH); 3.32 (s, 4H, CH$_2$OCH$_2$CO); 3.50–3.57 (m, 2H, NCH); 4.02 (s, 4H, CH$_2$OCH$_2$CO).

The mass spectrum gave: 602 (4,M$^+$), 381 (10), 380 (37, M$^+$—(CH$_2$CON(C$_6$H$_{11}$)$_2$)), 365 (6), 364 (4, M$^+$—(OCH$_2$CON(C$_6$H$_{11}$)$_2$)), 180 (5, N(C$_6$H$_{11}$)$_2$), 160 (24), 57 (100, (CH$_2$)$_3$CH$_3$), 29 (31, CH$_2$CH$_3$).

The NMR spectrum ($^{13}$C—NMR) in CDCl$_3$ gave: 7.7 (q, CH$_3$); 14.2 (q, CH$_3$); 23.6–31.4 (m, 24×CH$_3$ of the butyl-, ethyl - and cyclohexyl-substituents; 41.2 (s, C(CH$_2$)$_4$); 56.0 (d, 2×NCH(C$_5$H$_{10}$)); 57.3 (d, 2×NCH(C$_5$H$_{10}$)); 73.4 (t, 2×CH$_2$OCH$_2$CO); 74.2 (t, 2×CH$_2$OCH$_2$CO); 168.5 (s, 2×CO).

The analytical results were as follows:
calculated for C$_{37}$H$_{66}$N$_2$O$_4$; C=73.71, H=11.03, N=4.65,
found C=73.71, H=10.84, N=4.56.

EXAMPLE 2

According to the process described in example 1, the inventive compounds having the formulae II, III, IV and V were prepared. The diols used as starting material for the preparation of the compounds of formulae II, III and V were products of the Fluka AG, Switzerland, and the diol used as starting material for the preparation of the compound of formula IV was the corresponding product of the firm Aldrich, Steinheim, Federal Republic of Germany.

The chemical analysis of said four products is given below:

N,N,N',N'-tetracyclohexyl-5,5-dimethyl-3,7-dioxa-azelaic acid-diamide

Said product is the compound having the structural formula II stated before.
Calculated for the compound of formula C$_{33}$H$_{58}$N$_2$O$_4$;
C=72.53, H=10.70, N=5.13, found:
C=72.61, H=10.61, N=4.95.

N,N,N', N'-tetracyclohexyl-3,7-dioxa-acelaic acid diamide

Said product is the compound having the structural formula III stated before.
Calculated for the compound of formula C$_{31}$H$_{54}$N$_2$O$_4$;
C=71.77, H=10.49, N=5.40, found:
C=71.74, H=10.55, N=5.31.

N,N,N',N'-tetracyclohexyl-4-methyl-3,7-dioxa-azelaic acid-diamide

Said product is the compound having the formula IV stated before.
The analysis gave the following results:
calculated for the compound of formula C$_{32}$H$_{56}$N$_2$O$_4$:
C=72.14, H=10.59, N=5.26, found:
C=72.08, H=10.62, N=5.14.

N,N,N',N'-tetracyclohexyl-4-isopropyl-5,5-dimethyl-3,7-dioxa-azelaic acid-diamide Said product is the compound having the structural formula V stated before.
The analysis gave the following results:
Calculated for the compound of formula C$_{36}$H$_{65}$N$_2$O$_4$:
C=73.42, H=10.95, N=4.76, found:
C=73.09, H=10.76, N=4.70.

EXAMPLE 3

Preparation of the lithium complex of the N,N,N',N'-tetracyclohexyl-5,5-dimethyl-3,7-dioxa-azelaic acid-diamide The lithium complex of said inventive compound having the structural formula II stated before with lithium rhodanide of formula LiNCS was prepared.

300 mg (0.55 mmol) of the N,N,N',N'-tetracyclohexyl-5,5-dimethyl-3,7-dioxa-azelaic acid diamide and 17.8mg (0.27 mmol) of LiSCN (pract., Fluka AG) were dissolved in 4 ml of ethyl acetate (puriss., Fluka AG). Before its use the lithium-rhodanide was dried for 24 hours under high vacuum. The solution was allowed to stand in a flask with partly opened cap. Crystalline needles precipitated during the standing and said needles were filtered off.

100 mg (0.16 mmol) of said crystalline product were recovered, which corresponds to a yield of 29.7% of the theoretical yield.

The I.R. spectrum in chloroform showed peaks at 2080 cm$^{-1}$ and 1630 cm$^{-1}$.

The chemical analysis yielded the following results:
Calculated for the compound of formula C$_{33}$H$_{58}$N$_2$O$_4$.LiNCS: C=66.74, H=9.56, N=6.87 found:
C=66.89, H=9.64, N=6.95.

EXAMPLE 4

Preparation of a membrane for the quantitative determination of lithium ions in biological fluids The membrane was prepared according to the process described in the publication of P. Anker et al. in Anal. Chem. 1981, 53, 1970, mentioned before.

The used poly(vinylchloride) was the product "PVC S704 hochmolekular" produced by the Lonza AG, Visp, Switzerland, which is now available from the Fluka AG, Switzerland.

In all membranes the bis(1-butylpentyl) adipate was used as plasticizer. Said ester-plasticizer is the corresponding product purum p.a. which is available from the Fluka AG, Switzerland.

The following membranes were prepared:

| component | quantity in % by weight |
|---|---|
| Membrane 1 | |
| compound of formula II | 1.6 |
| plasticizer | 65.3 |
| poly(vinylchloride) | 33.1 |
| Membrane 2 | |
| compound of formula III | 1.7 |
| plasticizer | 65.3 |
| poly(vinylchloride) | 33.0 |
| Membrane 3 | |
| compound of formula IV | 1.8 |
| plasticizer | 65.6 |
| poly(vinylchloride) | 32.6 |
| Membrane 4 | |
| compound of formula V | 1.8 |
| plasticizer | 65.7 |
| poly(vinylchloride) | 32.5 |
| Membrane 5 | |
| compound of formula VI | 2.0 |
| plasticizer | 65.6 |
| poly(vinylchloride) | 32.4 |

The membranes 1, 2, 3, 4 and 5 are inventive membranes.

Furthermore a membrane for comparison was prepared in the same way using the same poly(vinylchloride) and the same plasticizer. In said membrane for comparison, however, the ion selective component was the prior art compound of formula B stated before.

| component | quantity in % by weight |
|---|---|
| Membrane for comparison | |
| compound of formula B | 1.2 |
| plasticizer | 66.9 |
| poly(vinylchloride) | 31.9. |

EXAMPLE 5

EMF-measurements

The electrolyte solutions for the potentiometric measurements were prepared with doubly quartz distilled water and chloride salts of highest purity. The corresponding products were the products purum p.a. or puriss. p.a. of Fluka AG, Buchs, Switzerland and the products pro analysis of E. Merck, Darmstadt, Federal Republic of Germany.

The used blood serum was obtained from the Medico-Chemical Central Laboratory, University Hospital, Zurich, Switzerland. In said blood serum the concentration of the sodium ions and the potassium ions as well as the total content of the calcium ions and the lithium ions were determined either by flame photometry or by atomic absorption spectrometry. According to said procedures in the used blood serum there was measured a concentration of lithium ions of 0.12 mmol/l.

The determination of the concentration of lithium ions with the inventive membranes was performed by adding to the blood serum small volumes of a solution which contains 0.05 mol of lithium chloride and 0.135 mol of sodium chloride. After each addition of a small volume of said solution containing lithium ions as well as sodium ions the serum was mixed for a short period and then sample volumes of 0.1 ml were taken and the EMF of said sample volumes determinated.

The EMF was measured with the macroelectrode as well as with the mini electrode described before, i.e. the small channel flow through electrode. More details of the EMF measurements were already given in the text before the present examples.

Said EMF-measurement showed that the inventive membranes 1, 2, 3, 4 and 5 described in example 4 have a sufficiently high selectivity for lithium ions over sodium ions so that in the serum samples the lithium concentration could be determined in the concentration ranges of clinical interests. Accordingly, with said membranes in the serum there could be determined lithium concentrations in the range of 0.7-1.5 mmol of lithium ions per liter in the presence of far higher concentrations of sodium ions, i.e. a background of 0.14 mol of sodium ions per liter.

The corresponding membrane for comparison which is as well described in example 4, however, had n sufficient selectivity for lithium ions and accordingly a determination of the lithium concentration in the above stated range was no longer possible when the above stated rather high concentrations of sodium ions were present in the corresponding sample solution.

The inventive membranes 1, 2, 3, 4 and 5 described in example 4 were suited for a quantitative determination of lithium ions in the serum samples. The stability of the measured values was good and furthermore the response time very short. Accordingly with said inventive membranes the final value of the EMF was already reached after 20-30 seconds. Said membranes, accordingly, are suited for a rapid and accurate determination of lithium ions in samples containing far higher concentrations of sodium ions.

The inventive membranes were used frequently and for several months for the determination of lithium concentrations in serum samples as well as in whole blood. During said time no ageing-problems occurred, i.e. the properties of said membranes did not deteriorate during said time.

What is claimed is:

1. A dicarboxylic acid diamide of formula I

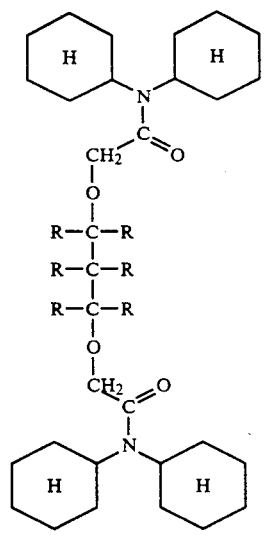

wherein each radical R is, independently of each other radical R, hydrogen, a straight chain or branched chain alkyl radical having 1-20 carbon atoms, a straight chain or branched chain alkenyl radical having 2-20 carbon atoms, or a straight chain or branched chain alkynyl radical having 2-20 carbon atoms.

2. A dicarboxylic acid diamide according to claim 1 wherein each radical R is, independently of each other radical R, hydrogen, a straight chain alkyl radical having 1-15 carbon atoms, or a branched chain alkyl radical having 1-15 carbon atoms.

3. A dicarboxylic acid diamide according to claim 2 wherein each R is, independently of each other R, hydrogen, a straight chain alkyl radical having 1-8 carbon atoms, or a branched chain alkyl radical having 1-8 carbon atoms.

4. A dicarboxylic acid diamide according to claim 1 wherein at least two of the R radicals are hydrogen.

5. A dicarboxylic acid diamide according to claim 2 wherein at least two of the R radicals are hydrogen.

6. A dicarboxylic acid diamide according to claim 5 which is a compound selected from the group of compounds having the following formulae II through VI:

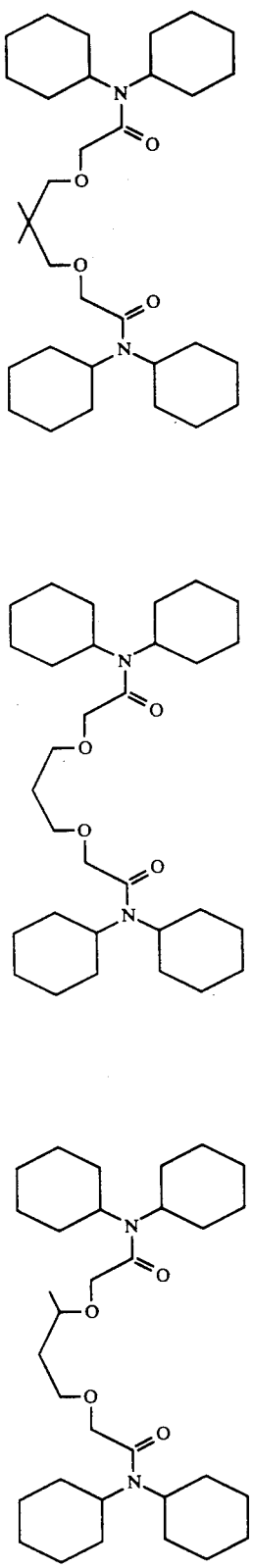

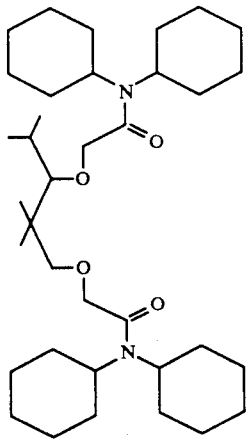

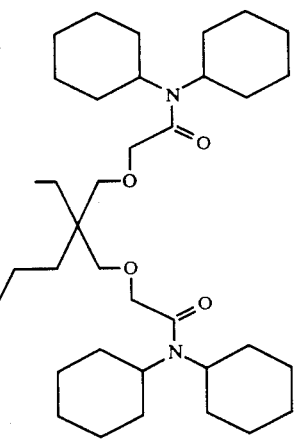

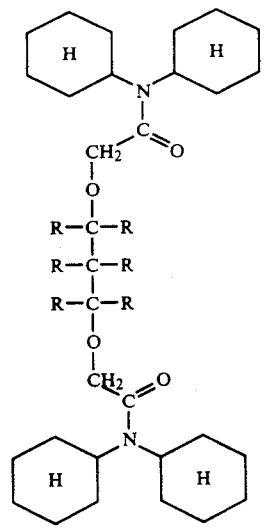

7. A complex comprising lithium and a dicarboxylic acid diamide of formula I:

$$\text{[Formula I]}$$

wherein each radical R is, independently of each other radical R, hydrogen, a straight chain or branched chain alkyl radical having 1-20 carbon atoms, a straight chain or branched chain alkenyl radical having 2-20 carbon atoms, or a straight chain or branched chain alkynyl radical having 2-20 carbon atoms.

8. A complex according to claim 7 wherein each radical R of the dicarboxylic acid diamide is, independently of each other radical R of said dicarboxylic acid diamide, hydrogen, a straight chain alkyl radical having 1-15 carbon atoms, or a branched chain alkyl radical having 1-15 carbon atoms.

9. A complex according to claim 8 wherein each radical R of the dicarboxylic acid diamide is, independently of each other radical R of said dicarboxylic acid diamide, hydrogen, a straight chain alkyl radical having 1-8 carbon atoms, or a branched chain alkyl radical having 1-8 carbon atoms.

10. A complex according to claim 9 wherein at least two R radicals of the dicarboxylic acid diamide are hydrogen.

11. A complex according to claim 8 wherein at least two R radicals of the dicarboxylic acid diamide are hydrogen.

12. A complex according to claim 11 wherein the dicarboxylic acid diamide is selected from the group of compounds having the formulae II through VI:

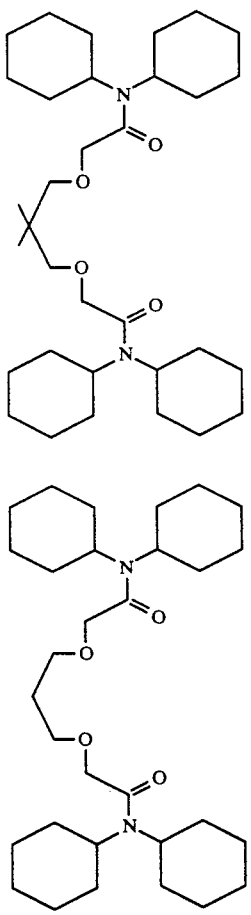

II

III

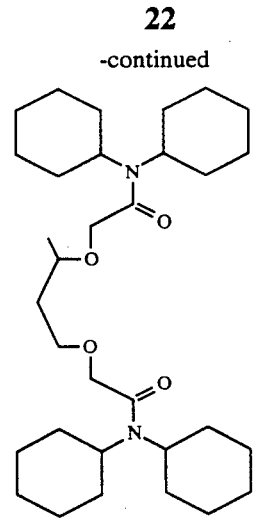

IV

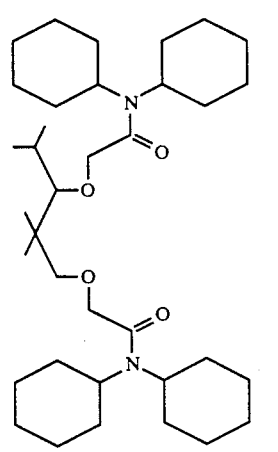

V

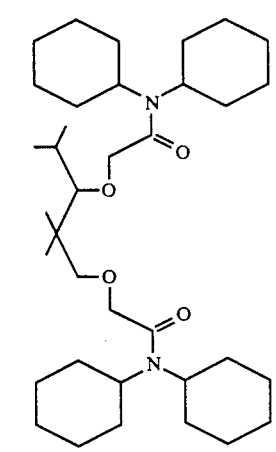

VI

13. A complex according to claim 7 formed from one mole of lithium ions and one mole of dicarboxylic acid diamide, which complex is soluble in lipophilic solvents.

14. A complex according to claim 13 in crystalline form.

* * * * *